United States Patent [19]

Kroener et al.

[11] Patent Number: 4,814,505

[45] Date of Patent: Mar. 21, 1989

[54] PURIFICATION OF N-VINYLFORMAMIDE

[75] Inventors: Michael Kroener, Mannheim; Willi Schmidt; Alfred Oftring, both of Ludwigshafen; Theo Proll, Bad Duerkheim; Heinrich Hartmann, Limburgerhof, all of Fed. Rep. of Germany

[73] Assignee: Basf Aktiengesellschaft, Rheinland-Pfalz, Fed. Rep. of Germany

[21] Appl. No.: 8,171

[22] Filed: Jan. 29, 1987

[30] Foreign Application Priority Data

Feb. 5, 1986 [DE] Fed. Rep. of Germany ....... 3603450

[51] Int. Cl.$^4$ ................ C07C 102/00; C07C 103/365; C07C 103/34
[52] U.S. Cl. .................................... 564/216; 564/123; 564/197
[58] Field of Search ........................ 564/216, 123, 197

[56] References Cited

U.S. PATENT DOCUMENTS

| | | | |
|---|---|---|---|
| 3,008,992 | 11/1961 | Lynn et al. | 564/216 X |
| 3,144,396 | 8/1964 | Lynn et al. | 534/216 X |
| 3,249,625 | 5/1966 | Bestian et al. | 534/123 X |
| 3,424,791 | 1/1969 | Kurtz et al. | 534/216 |
| 3,526,620 | 9/1970 | Bestian et al. | 534/123 X |
| 3,914,304 | 10/1975 | Schnabel et al. | 534/216 X |
| 4,421,602 | 12/1983 | Brunnmueller et al. | 162/168.2 |

FOREIGN PATENT DOCUMENTS

| | | | |
|---|---|---|---|
| 651791 | 11/1962 | Canada | 534/216 |
| 61-289069 | 12/1986 | Japan | 534/216 |

Primary Examiner—Floyd D. Higel
Attorney, Agent, or Firm—Oblon, Fisher, Spivak, McClelland & Maier

[57] ABSTRACT

N-Vinylformamide is purified by fractional distillation in the presence of formamide in a column under from 0.5 to 30 mbar by a method in which the distillation is controlled so that N-vinylformamide containing from 0.1 to 15% by weight of formamide is obtained as the distillate. Homopolymers having particularly high molecular weights can be prepared from the N-vinylformamide purified in this manner.

3 Claims, No Drawings

PURIFICATION OF N-VINYLFORMAMIDE

N-Vinylformamide can be prepared, for example, by the process of German Pat. No. 1,224,304, by eliminating hydrogen cyanide from formylalaninenitrile of the formula I

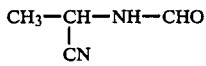

in the presence of a solid catalyst under reduced pressure at temperatures of, preferably, from 450° to 650° C. According to German Laid-Open Application DOS No. 2,336,977, N-vinylformamide is also obtained by eliminating methanol from N-alpha-methoxyethylformamide of the formula

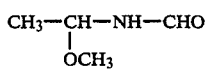

The N-vinylformamide obtained in each case by pyrolysis is distilled under reduced pressure. According to Example 9 of German Laid-Open Application DOS No. 2,336,977, distillation of the N-vinylformamide is carried out under 0.13 mbar and at a boiling point of 41° C. For economic reasons, such low pressures are not suitable for distillation on an industrial scale. Since N-vinylformamide is thermally very sensitive and readily polymerizes, poorer yields are obtained when higher pressures are used for the distillation of crude N-vinylformamide. In fact, higher pressures during the distillation necessitate higher bottom temperatures, which lead to substantial losses of monomer due to polymerization, not only in batch distillation but also in continuous distillation. Furthermore, the tendency of N-vinylformamide to polymerize cannot be adequately suppressed during the distillation even by adding a stabilizer, especially at fairly high temperatures.

N-Vinylformamide is used to prepare polymers which have superior properties compared with known assistants, for example in papermaking or the flocculation of sludges. This applies in particular to the high molecular weight polymers, although these can only be obtained where it is possible to use particularly pure N-vinylformamide as a starting material. Even very small amounts of impurities in the N-vinylformamide, which are difficult to identify analytically, give monomer grades from which it is impossible to prepare polymers having particularly high molecular weights, for example characterized by a Fikentscher K value higher than 160. For example, distillation of crude N-vinylformamide under 0.13 mbar gives only unsatisfactory monomer grades. On the other hand, it has been found that pure N-vinylformamide tends to undergo popcorn polymerization during prolonged distillation. Popcorn polymers of this type are crosslinked and therefore insoluble polymers which block the column.

It is an object of the present invention to provide a method for the purification of N-vinylformamide which gives N-vinylformamide in a quality which permits the preparation of polymers having particularly high molecular weights, which are characterized, for example, by the Fikentscher K values, the latter being higher than 160. During the distillation, polymerization should be avoided or should not present problems.

We have found that this object is achieved, according to the invention, by a process for the purification of N-vinylformamide by fractional distillation of N-vinylformamide in a column under reduced pressure, wherein the distillation is carried out in the presence of formamide under from 0.5 to 30 mbar, measured at the top of the column, and is controlled so that N-vinylformamide containing from 0.1 to 15% by weight of formamide is obtained as the distillate. The distillation is preferably controlled so that from 1 to 6% by weight of formamide remains in the distillate. Surprisingly, these formamide concentrations do not present problems in the subsequent polymerization of the N-vinylformamide to give polymers having particularly high K values, homopolymers of N-vinylformamide having a K value greater than 200 (determined by the Fikentscher method in 5% strength aqueous sodium chloride solution at 25° C. and at a polymer concentration of 0.1% by weight) being obtainable.

The novel process is primarliy used to purify crude N-vinylformamide which is obtained, for example, in the process for the preparation of N-vinylformamide described at the outset. It contains, in addition to the starting materials used in each case in the pyrolysis, i.e. a compound of the formula I or II, larger or smaller amounts of cleavage products from the pyrolysis. The novel process may also be used to purify N-vinylformamide which has been distilled by another method, in order to obtain a monomer from which polymers having particularly high molecular weights can be prepared.

The crude N-vinylformamide is purified by fractional distillation in a column under reduced pressure. Because of the thermosensitivity of the N-vinylformamide, the fractional distillation has to be carried out under reduced pressure. It is effected under from 0.5 to 30, preferably from 1 to 15, mbar, this being the pressure at the top of the column. An important feature of the present invention is that the fractional distillation is carried out so that the N-vinylformamide taken off as a distillate at the top of the column contains from 0.1 to 15% by weight, based on the N-vinylformamide used, of formamide. The crude N-vinylformamide used in the distillation contains from 1 to 70% by weight of formamide. Formamide is inert to N-vinylformamide and does not present problems in the polymerization when present in the purified N-vinylformamide in the stated concentrations. Formamide is preferably used in the distillation in an amount of from 5 to 50% by weight, based on N-vinylformamide. Depending on the crude product and on the requirements in respect of the purity of the N-vinylformamide, the number of theoretical plates of the particular columns used is from 5 to 40, preferably from 10 to 20. The distillation can be carried out batchwise by initially taking a solution of N-vinylformamide in formamide in a flask and removing the N-vinylformamide together with the small amounts of formamide stated above at the top of a column. However, the purification is preferably carried out continuously using formamide in such a way that a mixture of the N-vinylformamide to be purified and formamide is fed into the lower third to about the middle of a column, and N-vinylformamide together with, preferably, up to 6% by weight of formamide are separated off at the top of the column. In this procedure, a circulation for the bottom product is present at the bottom of the column, as is usual in distillation procedures. A circulating pump and an evaporator, preferably a falling film evaporator, are incorporated in this circulation as essential components. The formamide concomitantly used during the distillation is removed from the bottom, together with high boiling impurities and, where present, small amounts of N-vinylformamide. The formamide separated off from the bottom can, if required, be distilled and reused. Surprisingly, because formamide is employed, polymerization of the N-vinylformamide during distillation is completely or substantially avoided. The mixtures obtained as the distillate (N-vinylformamide containing from 0.1 to 15% by weight of formamide) can be polymerized in an aqueous medium at, preferably, from 30° to 100° C. In the presence of a polymerization initiator to give particularly high molecular weight poly-N-vinylformamides whose K value is greater than 200, for example from 205 to 270. Suitable polymerization processes in an aqueous medium are solution polymerization, water-in-oil polymerization and reverse suspension polymerization. Preferably, N-vinylformamide which contains from 1 to 6% by weight of formamide is polymerized by the water-in-oil polymerization method. The higher the K value of the homopolymers, the more effective are the products which can be prepared by eliminating the formyl group, for example when used as flocculants for sludges.

In the Examples, parts and percentages are by weight. The K values of the polymers were determined according to Fikentscher, Cellulose-Chemie, 13 (1932), 48–64 and 71–74, in 5% strength aqueous sodium chloride solution at 25° C. and at a polymer concentration of 0.1% by weight.

EXAMPLE 1

8.0 kg/hour of a mixture which consists of 60% of N-vinylformamide, 3% of components which have higher boiling points than N-vinylformamide and 37% of formamide are fed into the lower third of a continuous distillation plant which consists of a 4 m long column having a diameter of 150 mm and filled with Sulzer BX packing. At the top of the column, a pressure of 10 mbar is maintained and 2 g/hour of p-phenylenediamine dissolved in N-vinylformamide are metered in as a stabilizer.

With the aid of a circulating pump present at the bottom of the column, 400 l/hour of the bottom product are circulated under 19 mbar via a falling film evaporator heated at 140° C. In steady-state operation, a residence time of 1.0 hour and a temperature of 107° C. are established at the bottom. 3.1 kg/hour of 92.3% pure formamide containing 7.7% of high boilers are taken off as bottom product. 4.9 kg/hour of N-vinylformamide containing 2% of formamide are distilled off at the top of the column at a reflux ratio of 3:1.

In this procedure, virtually no N-vinylformamide is lost through polymerization. The formamide in the discharged bottom product can be recycled, if necessary after separating off the high boilers. The N-vinylformamide obtained in this manner can be polymerized by a water-in-oil emulsion polymerization method (cf. European Pat. No. 71,050) to prepare polymers having a K value of 210.

EXAMPLE 2

8.0 kg/hour of a mixture of 60% of N-vinylformamide, 35.2% of formamide, 1.8% of the compound of the formula II and 3.0% of high boilers are fed to the column stated in Example 1. Under conditions otherwise identical to those described in Example 1, 3.1 kg/hour of a mixture of 87.6% of formamide, 4.6% of a compound of the formula II and 7.7% of high boilers are taken off as bottom product at 107° C. 4.9 kg of a distillate consisting of 98% of N-vinylformamide and 2% of formamide are obtained at the top of the column. The purity of the N-vinylformamide achieved corresponds to the monomer quality of Example 1.

EXAMPLE 3

20.0 kg/hour of a mixture which consists of 61% of N-vinylformamide, 32% of formamide, 4.3% of a compound of the formula I and 2.7% of high boilers of unknown composition (such mixtures are obtained in the pyrolysis of compounds of the formula I) are fed into the lower third of a continuous distillation plant which consists of a 4 m long column having a diameter of 300 mm and filled with Sulzer BX packing. At the top of the column, a pressure of 3 mbar is maintained and 2 g/hour of p-phenylenediamine dissolved in N-vinylformamide are metered in as a stabilizer. With the aid of a circulating pump present at the bottom of the column, 800 l/hour of the bottom product are circulated under 13 mbar via a falling film evaporator heated at 140° C. In the steady state, 7.6 kg/hour of a mixture of 81.6% of formamide, 11.3% of a compound of the formula I and 7.1% of high boilers are removed as bottom product at 103° C. 12.4 kg/hour of a distillate consisting of 98.4% of N-vinylformamide and 1.6% of formamide are obtained at the top of the column, at a reflux ratio of 3:1.

The N-vinylformamide obtained in this manner can be polymerized by a water-in-oil emulsion polymerization procedure (cf. European Patent No. 71,050) to prepare homopolymers having a high K value if, for example, 402.3 g of distilled water, 4.99 g of potassium dihydrogen phosphate and 0.164 g of sodium hydroxide are initially taken in a 2 liter 4-necked flask provided with a stirrer, a thermometer, a nitrogen inlet tube and a condenser, and a mixture of 339.98 g of a hydrocarbon mixture (mixture of 84% of saturated aliphatic hydrocarbons and 16% of naphthenic hydrocarbons having a boiling range of from 192° to 254° C.) and 39.45 g of an emulsifier (reaction product of 1 mole of oleyl glycidyl ether, 1 mole of glycerol and 2 moles of ethylene oxide, prepared as described in German Laid-Open Application DOS No. 2,557,324) is added with stirring and 213.5 g of the purified N-vinylformamide obtained as described in Example 3 are then introduced. Nitrogen is then passed through the stirred mixture for 1 hour at room temperature, after which the mixture is heated to 45° C. while stirring at a speed of 300 rpm, and 0.106 g of 2,2'-azobis(2,4-dimethylvaleronitrile) dissolved in 0.226 g of acetone is added. The reaction mixture is then heated to 60° C. while stirring continuously, and is polymerized at from 60° to 65° C. in the course of about 2 hours. Thereafter, a further 0.106 g of 2,2'-azobis(2,4-dimethylvaleronitrile) dissolved in 0.226 g of acetone is added, and the reaction mixture is kept at 60° C. for a further 2 hours to continue polymerization. The solids content of the polymer emulsion is determined by precipitating the polymer in acetone and is found to be 20.4%. The K value of the polymer is 248.

COMPARATIVE EXAMPLE 1

8.0 kg/hour of a mixture of 95% of N-vinylformamide, 2.5% of a compound of the formula I and 2.5% of high boilers are metered into the column stated in Example 1. A pressure of 10 mbar is maintained at the top of the column. 400 l/hour of bottom product are circulated by means of the circulating pump. The falling film evaporator must be kept at 170° C.

A reflux ratio of 3:1 is established at the top of the column. Under these conditions, 6.35 kg/hour of pure N-vinylformamide can be distilled off. Under steady-state conditions, a residence time of 1.9 hours is established in the bottom under a pressure of 19 mbar and at 140° C. 1.65 kg/hour of bottom product are removed from the bottom. In addition to the original 0.2 kg of compound of the formula I and 0.2 kg of high boilers, this product contains 1.15 kg of oligomers and polymers of N-vinylformamide and 0.1 kg of monomeric N-vinylformamide, corresponding to a content of 6%. Hence, 15.1% of the N-vinylformamide originally present are lost through polymerization. In addition, a further 1.3% of N-vinylformamide out of the amount originally present are removed as monomer together with the bottom product. After operation for 28 hours, the pressure loss in the column increases as a result of incipient popcorn polymerization. After a further 3 hours, the column is blocked by polymerization.

COMPARATIVE EXAMPLE 2

8.0 kg of a mixture of 92% of N-vinylformamide, 3% of a compound of the formula II and 5% of high boilers are fed to the column, using a procedure similar to that described in Comparative Example 1. 6.22 kg/hour of pure N-vinylformamide are distilled off at the top of the column. Under steady-state conditions, a residence time of 1.7 hours and a temperature of 140° C. are established at the bottom. 1.78 kg/hour of bottom product are discharged. In addition to the original content of a compound of the formula II and high boilers, this product contains 1.1 kg of oligomers and polymers as well as 2% by weight of monomeric N-vinylformamide. Hence, a total of 15.4% of the N-vinylformamide fed in are lost.

COMPARATIVE EXAMPLE 3

Adiabatic heat accumulation test under pressure with N-vinylformamide 80 g of pure N-vinylformamide are heated to 100° C. in an autoclave equipped with a bursting disk. During this procedure, the pressure reaches 2 bar. To reduce heat losses, the oven temperature is adjusted to the product temperature during the exothermic reaction which begins after about 1 hour. The product temperature reaches 136° C. after storage for 1.5 hours, and 282° C. after a further 10 minutes, the pressure increasing to above 50 bar and the bursting disk being triggered.

The heat accumulation test under pressure shows that N-vinylformamide is thermally very sensitive and that there is a danger of explosive polymerization on heating.

We claim:

1. A process for purifying N-vinylformamide by fractional distillation of N-vinylformamide in a column under reduced pressure, wherein the distillation is carried out in the presence of formamide under from 0.5 to 30 mbar, measured at the top of the column, and the distillation is controlled so that N-vinylformamide containing from 0.1 to 15% by weight of formamide is obtained as the distillate.

2. A process as claimed in claim 1, wherein the distillation is carried out continuously under from 0.5 to 30 mbar, measured at the top of the column, so that N-vinylformamide containing from 1 to 6% by weight of formamide is obtained as the distillate.

3. A process as claimed in claim 1, wherein the distillation is carried out in the presence of from 1 to 70% by weight, based on the N-vinylformamide used, of formamide.

* * * * *